United States Patent
Suzuki (10) Patent No.: US 6,678,040 B1
(45) Date of Patent: Jan. 13, 2004

(54) APPARATUS FOR MEASURING NUMBER OF CELLS

(75) Inventor: Atsushi Suzuki, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 387 days.

(21) Appl. No.: 09/608,106

(22) Filed: Jun. 30, 2000

(30) Foreign Application Priority Data

Jul. 2, 1999 (JP) ............................................ 11-189490

(51) Int. Cl.$^7$ .......................... G01N 33/48; G01N 9/30; B01D 37/00
(52) U.S. Cl. .............................. 356/39; 210/767; 422/72
(58) Field of Search .......................... 356/39, 335, 336, 356/338, 337, 441; 250/461.2, 462.1, 483.1, 484.2, 559.4, 559.41, 559.44; 210/739, 96.1, 767, 646, 787; 604/4.01; 422/55, 63, 67, 72

(56) References Cited

U.S. PATENT DOCUMENTS

| | | | |
|---|---|---|---|
| 4,810,090 A | | 3/1989 | Boucher et al. |
| 4,939,081 A | | 7/1990 | Figdor et al. |
| 5,047,321 A | * | 9/1991 | Loken et al. ................. 435/6 |
| 5,059,395 A | * | 10/1991 | Brittenham et al. .......... 422/73 |
| 5,125,737 A | * | 6/1992 | Rodriguez et al. ........... 365/39 |
| 5,316,667 A | * | 5/1994 | Brown et al. ................ 210/85 |
| 5,351,118 A | * | 9/1994 | Spinell ........................ 356/72 |
| 5,360,542 A | * | 11/1994 | Williamson et al. ........ 210/232 |
| 5,451,525 A | * | 9/1995 | Shenkin et al. .............. 436/63 |
| 5,469,375 A | * | 11/1995 | Kosaka ....................... 364/555 |
| 5,483,469 A | * | 1/1996 | Van den Engh et al. .... 364/555 |
| 5,488,469 A | * | 1/1996 | Yamamoto et al. .......... 356/72 |
| 5,505,685 A | * | 4/1996 | Antwiler ...................... 494/37 |
| 5,598,842 A | * | 2/1997 | Ishihara et al. ............ 128/637 |
| 5,639,382 A | * | 6/1997 | Brown ....................... 210/739 |
| 5,703,959 A | * | 12/1997 | Asano et al. .............. 382/133 |
| 5,719,666 A | * | 2/1998 | Fukuda et al. ............... 356/72 |
| 5,731,867 A | * | 3/1998 | Katayama .................... 356/73 |
| 5,737,078 A | * | 4/1998 | Takarada et al. ............ 356/338 |
| 5,769,811 A | * | 6/1998 | Stacey et al. .............. 604/4.01 |
| 5,798,827 A | * | 8/1998 | Frank et al. ................. 356/39 |
| 5,830,701 A | * | 11/1998 | Houwen et al. ............. 435/29 |
| 5,833,866 A | * | 11/1998 | Brown ....................... 210/739 |
| 5,946,220 A | * | 8/1999 | Lemelson .............. 364/528.08 |
| 5,958,250 A | * | 9/1999 | Brown et al. .............. 210/745 |
| 6,025,201 A | * | 2/2000 | Zelmanovic et al. ......... 436/63 |
| 6,114,173 A | * | 9/2000 | Zelmanovic et al. ......... 436/63 |
| 6,118,522 A | * | 9/2000 | Kanai et al. ................. 356/73 |
| 6,228,652 B1 | * | 5/2001 | Rodriguez et al. ........... 436/63 |
| 6,317,511 B1 | * | 11/2001 | Horiuchi ..................... 382/133 |
| 6,319,471 B1 | * | 11/2001 | Langley et al. .............. 422/67 |
| 6,334,842 B1 | * | 1/2002 | Hlavinka et al. ............. 494/36 |
| 6,497,674 B1 | * | 12/2002 | Steele et al. .............. 604/6.01 |

FOREIGN PATENT DOCUMENTS

LU            84604 A     10/1984

* cited by examiner

*Primary Examiner*—Zandra V. Smith
*Assistant Examiner*—Gordon J Stock, Jr.
(74) *Attorney, Agent, or Firm*—Burns, Doane, Swecker & Mathis, LLP (57) ABSTRACT

A number-of-cells measuring apparatus for measuring the number of cells contained in a liquid including cells comprises an input section for inputting information of a size of said pre-measured cells; a duct through which said liquid flows; a measuring section installed on said duct and measuring a concentration of said cells contained in said liquid flowing through said duct; and an information processing section processing information of the size of said cells inputted thereto from said input section, information of a flow rate of said liquid flowing through said duct, and information of the concentration of said cells obtained by said measuring section, wherein said information processing section has a function of computing the number of cells which have passed through said measuring section, based on the flow rate of said liquid, the concentration of said cells, and the size of said cells or a numerical value in which the size of said cells is considered.

15 Claims, 7 Drawing Sheets

APPARATUS FOR MEASURING NUMBER OF CELLS

BACKGROUND OF THE INVENTION

The present invention relates to an apparatus for measuring the number of cells contained in a liquid to be examined. More particularly, the present invention relates to an apparatus for measuring the number of blood cells or platelets contained in blood components.

By present when collecting bloods, to effectively utilize collected blood and reduce donor's burden, the collected blood is separated into various components centrifugally and components required for a donee are collected, whereas remaining components are returned to the donor.

In obtaining a platelet product in this blood component collection process, the blood donated from the donor is introduced to a blood component separation circuit to separate it into four components of plasma, white blood cells, platelets, and red blood cells by a centrifugal separator called a centrifugal bowl installed in the blood component separation circuit. Then, the platelets are collected in a container such as a bag to produce a platelet product, and the remaining components, namely, the plasma, the white cells, whereas the red blood cells are returned to the donor. To secure a possible largest number of platelets, a series of the processes of donating blood from the donor, centrifugally separating the gathered blood into the blood components, collecting the platelets, and returning the blood to the donor is repeatedly performed.

In this case, it is necessary to know the number of platelets in the obtained platelet product. To this end, after all the processing terminates, sampling of a mixture of thick platelets and plasmas collected in the bag is performed, and the number of the platelets is measured to compute the number of the entire platelets in the bag.

However, in this method, it is impossible to know the amount of gathered platelets in the process of donating the blood from the donor and treating the blood. Therefore, it is impossible to determine whether a target value (for example, 5, 10, 15 or 20 units of platelets) of the platelets has been attained. Such being the case, it may occur that the platelets are excessively donated from the donor, which increases donor's burden.

SUMMARY OF THE INVENTION

The object of this invention is to provide a number-of-cells measuring apparatus for measuring the number of cells contained in a liquid including cells which comprises an input section for inputting information of a size of a pre-measured cells, a duct through which said liquid flows, a measuring section installed on said duct and measuring a concentration of said cells contained in said liquid flowing through said duct, and an information processing section processing information of the size of said cells inputted thereto from said input section, information of a flow rate of said liquid flowing through said duct, and information of the concentration of said cells obtained by said measuring section, wherein said information processing section has a function of computing the number of cells which have passed through said measuring section, based on the flow rate of said liquid, the concentration of said cells, and the size of said cells or a numerical value in which the size of said cells is considered.

The object of this invention is to provide a number-of-cells measuring apparatus for measuring the number of cells contained in a liquid including cells which comprises an input section for inputting information of a size of a pre-measured cells, a duct through which said liquid flows, a measuring section installed on said duct and measuring a concentration of said cells contained in said liquid flowing through said duct, and an information processing section processing information of the size of said cells inputted thereto from said input section, information of a flow rate of said liquid flowing through said duct, and information of the concentration of said cells obtained by said measuring section, wherein said information processing section has a computing function of computing a prior-to-correction number of cells which have passed through said measuring section, based on the flow rate of said liquid and the concentration of said cells; and a correction value computing function of correcting a prior-to-correction number of said cells computed by said computing function by taking the size of said cells into consideration.

The object of this invention is to provide a number-of-cells measuring apparatus for measuring the number of platelets of blood components flowing out from an outflow port of a centrifugal separator, for centrifugally separating a blood into a plurality of said blood components, comprising a rotatable rotor having a blood storage space formed therein and an inflow port and said outflow port both communicating with said blood storage space into which said blood is introduced from said inflow port, comprising an input section for inputting information of a size of said pre-measured platelets, a duct connected with said outflow port, a measuring section installed on said duct and measuring a concentration of said platelets of said blood components flowing through said duct; and an information processing section processing information of the size of said platelets inputted thereto from said input section, information of a flow rate of said blood components flowing through said duct, and information of the concentration of said platelets obtained at said measuring section, Wherein said information processing section has a function of computing the number of platelets which have passed through said measuring section, based on the flow rate of said blood components, the concentration of said platelets, and the size of said platelets or a numerical value in which the size of said platelets is considered.

The object of this invention is to provide a number-of-cells measuring apparatus for measuring the number of platelets of blood components flowing out from an outflow port of a centrifugal separator, for centrifugally separating a blood into a plurality of said blood components, comprising a rotatable rotor having a blood storage space formed therein and an inflow port and said outflow port both communicating with said blood storage space into which said blood is introduced from said inflow port, comprising, an input section for inputting information of a size of said pre-measured platelets, a duct connected with said outflow port, a measuring section installed on said duct and measuring a concentration of said platelets of said blood components flowing through said duct; and an information processing section processing information of the size of said platelets inputted thereto from said input section, information of a flow rate of said blood components flowing through said duct, and information of the concentration of said platelets obtained at said measuring section, wherein said information processing section has a computing function of computing a prior-to-correction number of platelets which have passed through said measuring section, based on the flow rate of said blood components and the concentration of said platelets; and a correction value computing function of correcting a prior-to-correction number of said platelets computed by said computing function by taking the size of said platelets into consideration.

DETAILED DESCRIPTION OF THE PREFERRED EMBODIMENTS

A number-of-cells measuring apparatus according to the present invention will be described with reference to embodiments shown in the accompanying drawings.

Figure 1:
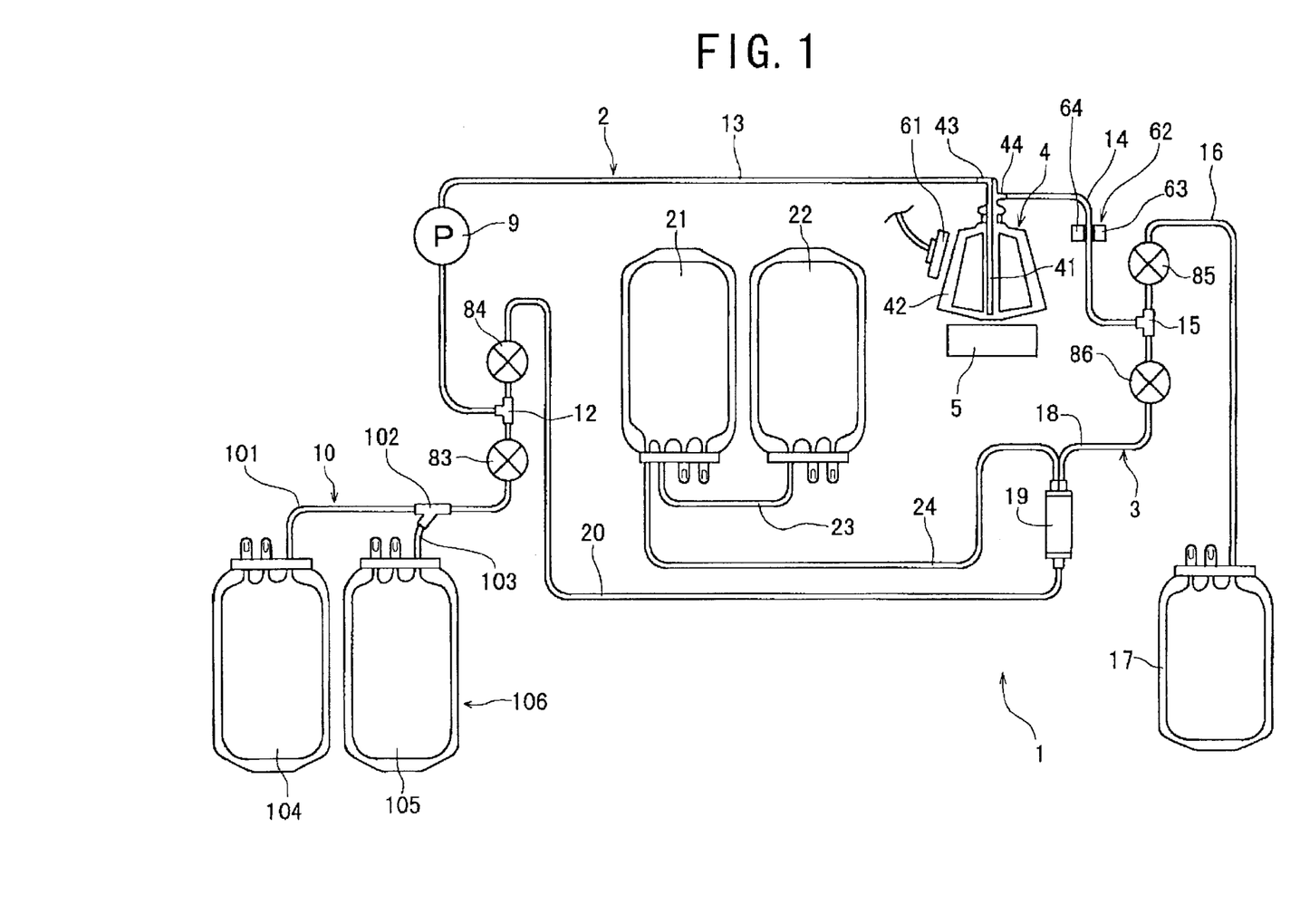
FIG. 1 is a schematic drawing of an example of the construction of a blood component separation apparatus on which the number-of-cells measuring apparatus of the present invention is installed.
Figure 2:
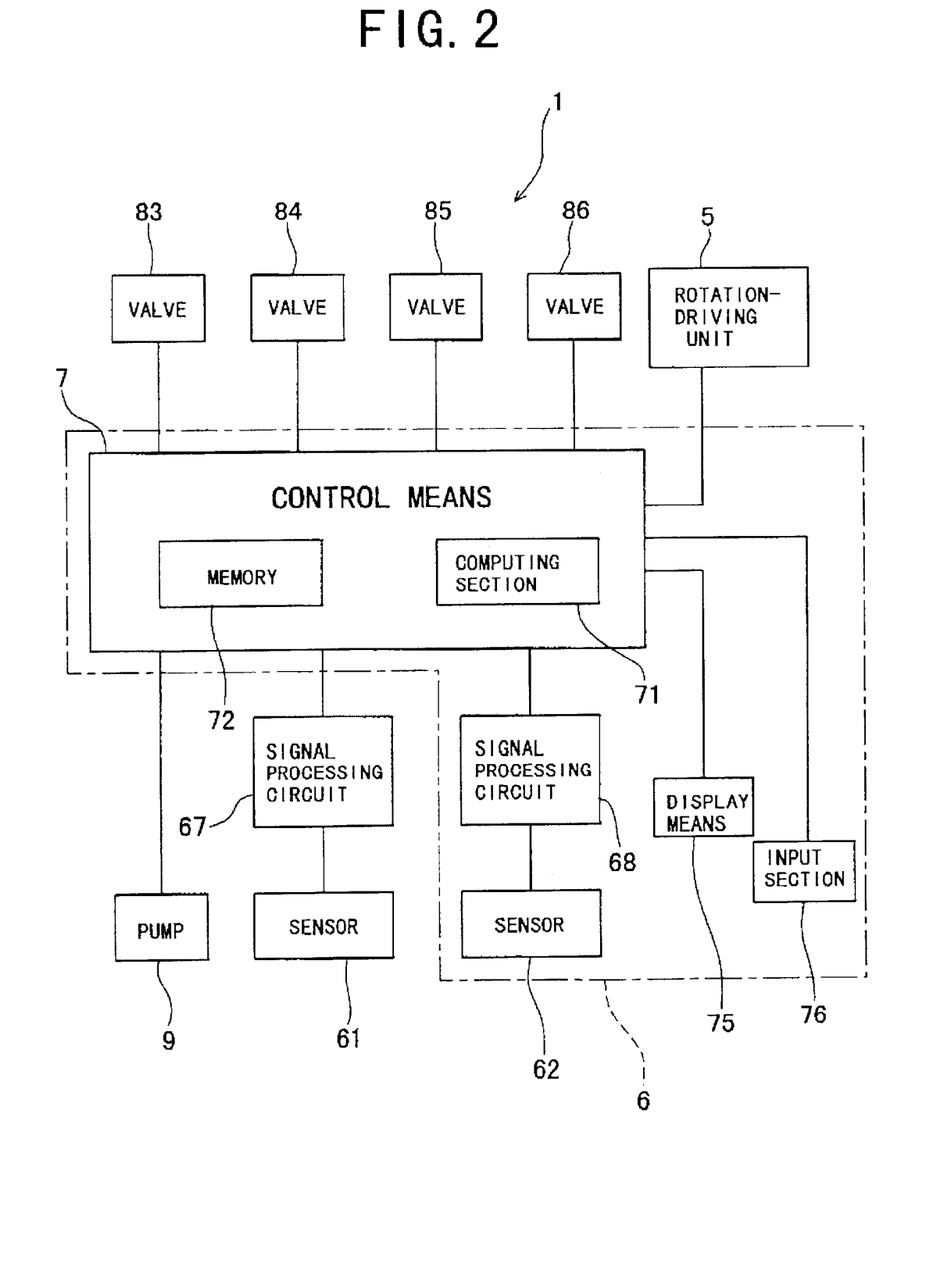
FIG. 2 is a block diagram showing a control system of the blood component separation apparatus shown in FIG. 1.

FIG. 1 shows an example of the construction of a blood component separation apparatus on which the number-of-cells measuring apparatus of the present invention is mounted. FIG. 2 is a block diagram showing the control system of the blood component separation apparatus shown in FIG. 1. Initially, the entire construction of the blood component separation apparatus will be described below with reference to FIGS. 1 and 2.

The blood component separation apparatus 1 includes a centrifugal bowl 4 (in other words, centrifugal separator), a rotation-driving unit 5 for driving the centrifugal bowl, a first line 2 (in other words, line for introducing blood or plasma) for selectively introducing blood and plasma into the centrifugal bowl 4, a second line (in other words, blood component collection line) 3 for collecting blood components separated by the centrifugal bowl 4, an optical sensor 61 detecting an interface between the blood components, an optical sensor 62 detecting the concentration of a platelet, a control section (in other words, control means) 7, a third line 10 (in other words, line for donating blood from donor and returning blood thereto) having a blood storage portion 106, a pump 9 (in other words, liquid feeding means) installed on the first line 2, and display section (in other words, display means) 75.

As shown in FIG. 1, the third line 10 includes a tube 101, a tube 103 connected to the tube 101 through a branch connector 102 mounted on the tube 101, and blood bags 104, 105 connected to the front end of the tubes 101, 103, respectively. The blood bags 104, 105 constitute the blood storage portion 106.

The rear of the tube 101 is connected with one end of each of tubes 13, 20 through a T-shaped branch connector 12. A valve 83 serving as a duct opening/closing means for cutting off and releasing an inner duct of the tube 101 is mounted on the tube 101.

The first line 2 includes the tube 13 and the branch connector 12 connected with one end of the tube 13. The other end of the tube 13 is connected with an inflow port 43 of the centrifugal bowl 4. A blood-feeding pump 9 (for example, roller pump) is installed on the tube 13.

Figure 3:
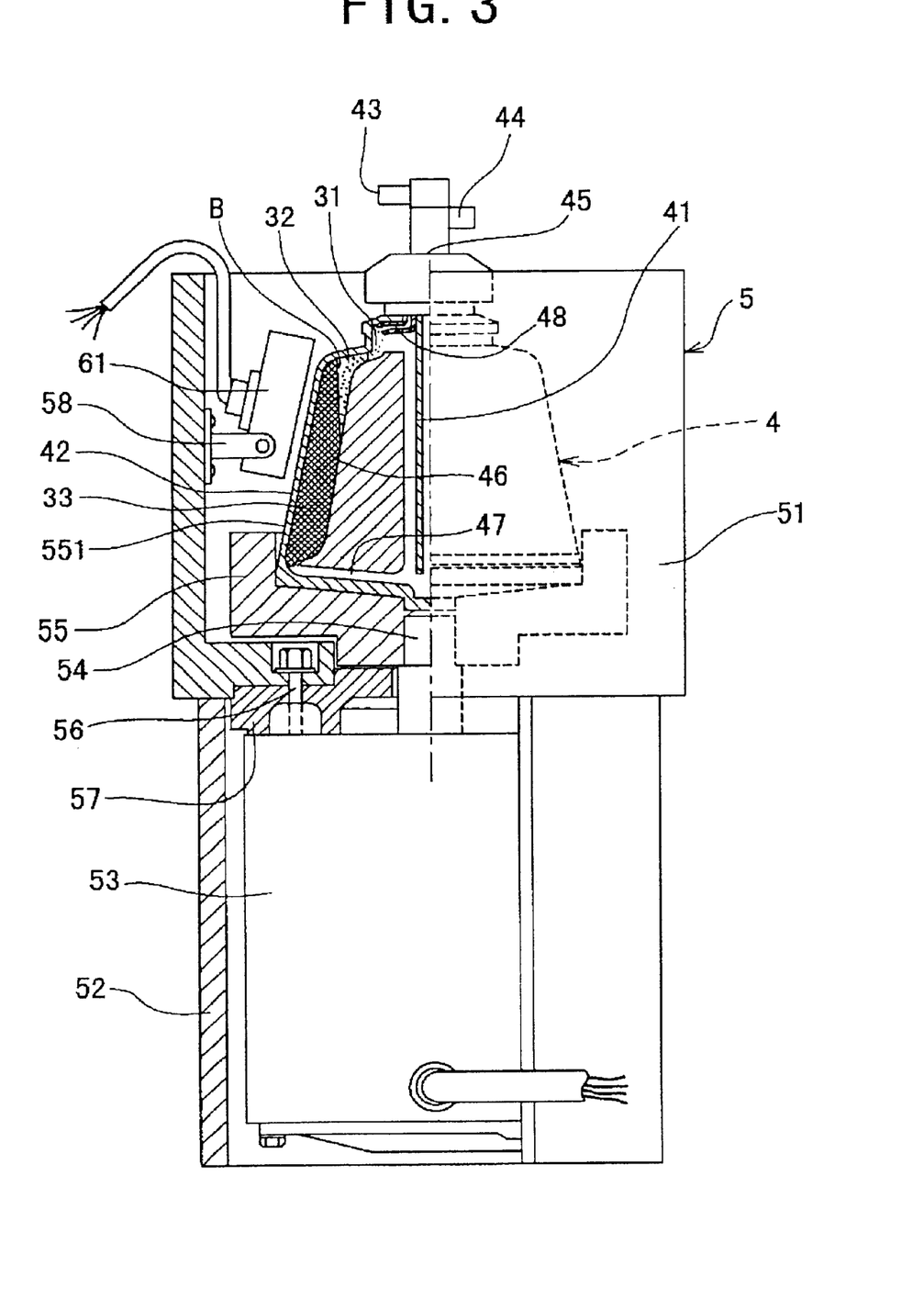
FIG. 3 is a partial sectional front view showing an example of the construction of a centrifugal bowl and a rotation-driving unit of the blood component separation apparatus of FIG. 1.

As shown in FIG. 3, the centrifugal bowl 4 includes a vertically extending tubular member 41 having the inflow port 43 formed at its upper end and a rotor 42 rotating around the tubular member 41 and liquid-tightly sealed from an upper part 45 of the centrifugal bowl 4. An annular blood storage space 46 is formed along the inner surface of the peripheral wall of the rotor 42. The blood storage space 46 is so tapered that its inner and outer diameters decrease gradually from its lower portion to the upper portion. The lower portion of the blood storage space 46 communicates with an opening formed at the lower end of the tubular member 41 through an approximately disk-shaped duct 47 formed along the bottom portion of the rotor 42. The upper portion of the blood storage space 46 communicates with an outflow port 44 through a duct 48. In the rotor 42, the volume of the blood storage space 46 is set to 100–350 ml.

The rotation-driving unit 5 rotates the rotor 42 in a predetermined centrifugal condition (in other words, rotation speed and rotation time period). The separation pattern (for example, number of blood components to be separated) of blood in the rotor 42 can be set by the centrifugal condition. In the embodiment, as shown in FIG. 3, the centrifugal condition is so set that in the duct of the rotor 42, blood is separated into a plasma layer 31 (in other words, inner layer), a buffy coat layer 32 (in other words, intermediate layer), and a red blood cell layer 33 (in other words, an outer layer).

As shown in FIG. 3, the rotation-driving unit 5 includes a housing 51 accommodating the centrifugal bowl 4, a leg part 52, a motor 53 serving as the driving source, a disk-shaped fixing base 55 holding the centrifugal bowl 4.

The housing 51 is fixed to the upper portion of the leg part 52. The 1motor 53 is fixed to the lower surface of the housing 51 with a bolt 56 through a spacer 57. The fixing base 55 is fitted on the upper end of a rotation shaft 54 of the motor 53, such that the fixing base 55 is coaxial with the rotation shaft 54 and rotates together with the rotation shaft 54. A concave portion 551 in which the bottom portion of the rotor 42 is fitted is formed on the upper portion of the fixing base 55. The upper part 45 of the centrifugal bowl 4 is fixed to the housing 51 with a fixing member not shown in FIG. 3.

In the rotation-driving unit 5, with the start of the motor 53, the fixing base 55 and the rotor 42 fixed thereto rotate at a rotation speed of 3000–6000 rpm.

The optical sensor 61 is fixedly installed on the inner wall of the housing 51 with an installing member 58. The optical sensor 61 optically detects the interface between separated blood components in the rotor 42, namely, the position of an interface B between the buffy coat layer 32 and the red blood cell (in other words, thick red blood cell) layer 33. As the optical sensor 61, a line sensor capable of accomplishing vertical scanning along the peripheral surface of the rotor 42 is used. That is, the optical sensor 61 has a plurality of light-emitting elements such as light-emitting diodes (LED) arranged in rows and a plurality of light-receiving elements such as photodiodes arranged in rows. In this construction, the light-receiving elements receive light reflected from blood components after it is emitted from the light-emitting elements. The amount of light received by the light-receiving elements is photoelectrically converted. The intensity of the reflected light from the buffy coat layer 32 is different from that reflected from the red blood cell layer 33 separated from the buffy coat layer 32. A position corresponding to the light-receiving element at which the amount of the received light, namely, an output voltage has changed is detected as the position of the interface B.

As shown in FIG. 1, the outflow port 44 of the centrifugal bowl 4 is connected with one end of the tube 14. The other end of the tube 14 is connected with one end of each of tubes 16, 18 through a T-shaped branch connector 15.

The other end of the tube 16 is connected with a platelet bag 17. A valve 85 opening and closing the duct in the tube 16 is installed on the tube 16.

The other end of the tube 18 is connected with a bubble-removing chamber 19. A valve 86 opening and closing the duct in the tube 18 is installed on the tube 18.

The end of a tube 20 whose one end is connected with the branch connector 12 is connected with the bubble-removing chamber 19. A valve 84 opening and closing the duct in the tube 20 is installed on the tube 20.

An air storage bag 22 stores exhausts air from a plasma bag 21 after a series of operations terminates. Thus, the plasma bag 21 and the air storage bag 22 are connected with a tube 23 to communicate the interiors of both with each other. The plasma bag 21 is connected with one end of the tube 24. The other end of the tube 24 is connected with the bubble-removing chamber 19.

In this construction, the second line 3 is constructed of the tubes 14, 16, 18,20, 23, and 24 and the branch connector 15, the chamber 19, the bags 17, 21, and 22. The tube 18, the chamber 19, the tubes 23, 24, and the bags 21, 22 constitute a plasma-collecting branch line for collecting plasmas. The tubes 14, 16 and the platelet bag 17 constitute a platelet-collecting branch line for collecting the platelets.

Although not shown, the blood component separation apparatus 1 may be so constructed that the plasma bag 21 can selectively direct the end of the tube 24 at its connection side upward or downward.

Figure 4:
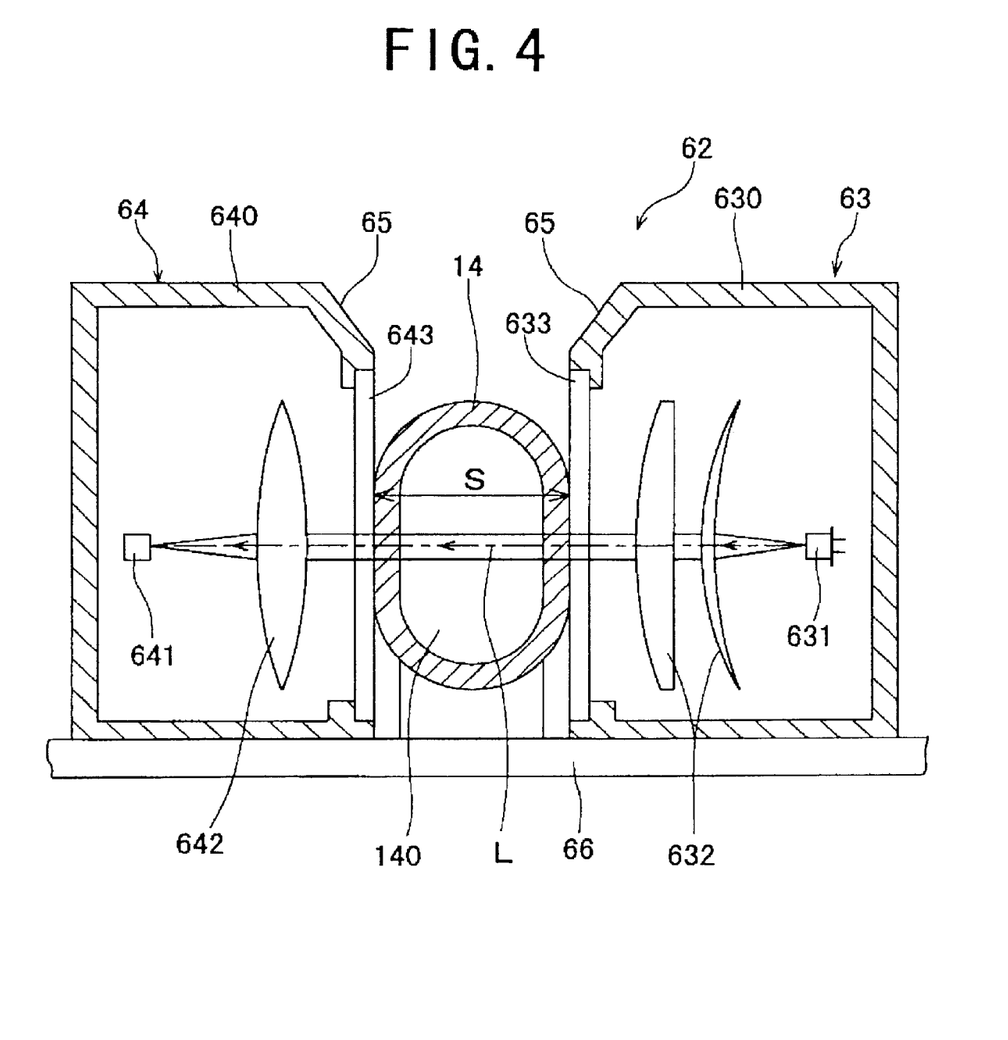
FIG. 4 is a sectional front view showing an example of the construction of a measuring section (optical sensor).

The optical sensor 62 is installed on the tube 14. The optical sensor 62 serves as a measuring section for measuring the concentration of platelets contained in the blood component (in other words, liquid to be examined) flowing through a duct 140 formed in the tube 14. FIG. 4 is a vertical sectional view showing the construction of the optical sensor 62. As shown in FIG. 4, the optical sensor 62 includes a light-projecting portion 63 and a light-receiving portion 64 opposed to each other, with the tube 14 interposed therebetween.

The light-projecting portion 63 has a casing 630 in which a light source 631 and a collimator lens 632 are installed. The light-receiving portion 64 has a casing 640 in which a condenser lens 642 and a light-receiving element 641 such as a photodiode are installed. Transparent plates 633 and 643 opposed to each other and sandwiching the tube 14 therebetween are installed on the light-projecting portion 63 and the light-receiving portion 64, respectively. A tapered guide portion 65 guiding the tube 14 when the tube 14 is installed between the transparent plates 633 and 643 is formed above the transparent plates 633 and 643, respectively. The light-projecting portion 63 and the light-receiving portion 64 are fixed to a base 66 to keep the interval S between the transparent plates 633 and 643 constant.

The interval S between the transparent plates 633 and 643 is set smaller than the outer diameter of the tube 14. Thereby, the duct 140 of the circular tube 14 is made flat or oval, with the tube 140 sandwiched between the transparent plates 633 and 643. Thus, it is possible to allow the optical length of laser beams L in the duct 140 to be constant even though the tube 14 is displaced slightly in the vertical direction in FIG. 4 and accomplish measurement of concentration with high accuracy.

The interval S is set to favorably 50–99% and more favorably 80–90% of the sectional outer diameter of the tube 14. The reason is as follows: If the interval S exceeds 99% thereof, the effect to be brought about by the flat or oval configuration of the tube 14 cannot be obtained, whereas if the interval S is less than 50% thereof, a resistance to the flow of the blood component increases.

The interval S may be changed. For example, when the number of red blood cells is measured, it is preferable to set the interval S smaller in correspondence to the sensitivity of the optical sensor 62.

The collimator lens 632 collimates laser beams L emitted from the light source 631 of the light-projecting portion 63. After the laser beams L pass through the transparent plate 633 and the wall of the tube 14, they pass through the duct 140 and then the wall of the tube 14 and the transparent plate 643. Then, the laser beams L are condensed on the light-receiving surface of the light-receiving element 641. In this case, the light-receiving element 641 outputs an electric signal having a voltage corresponding to an amount of received light. The transmittance of the laser beams L in the duct 140 changes in correspondence to a concentration of the platelet in the blood component. Therefore, it is possible to detect the change of the concentration of the platelet as the change of a voltage outputted from the light-receiving element 641.

It is preferable to set the diameter of the laser beams L to 0.5–2 mm when the laser beams L pass through the duct 140.

Figure 5:
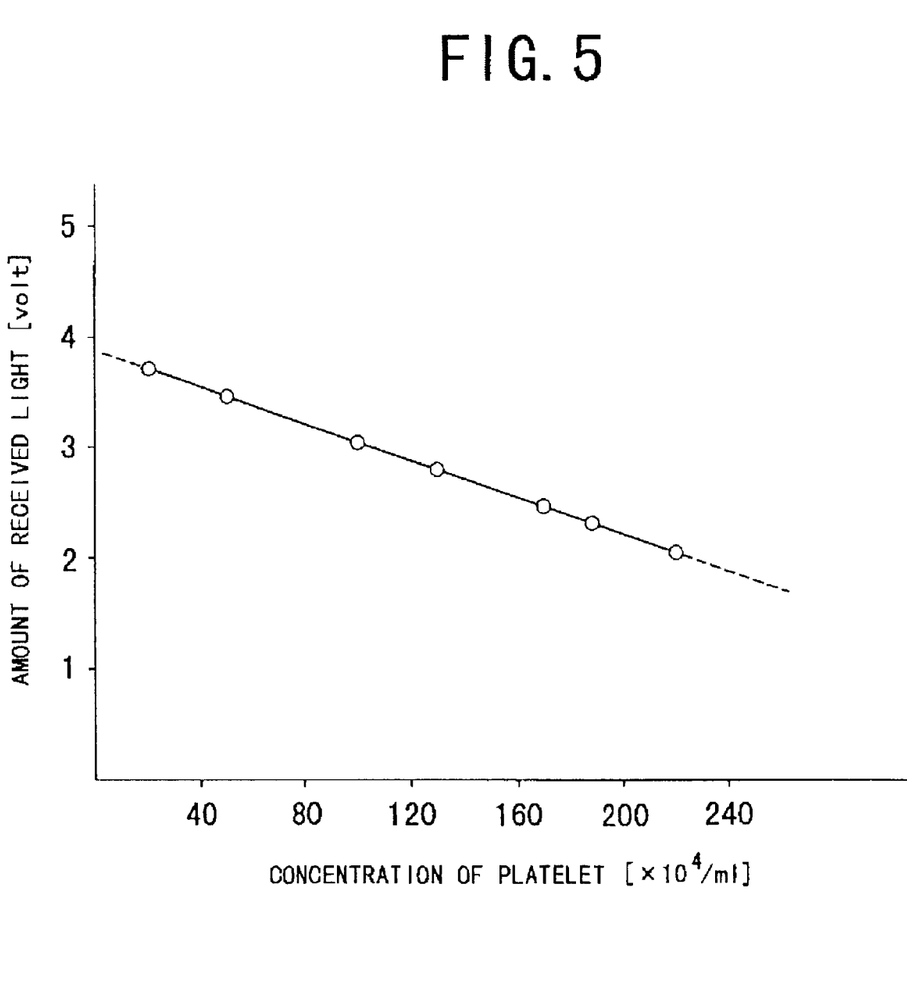
FIG. 5 is a graph showing the relationship between the concentration of platelets in blood components at the measuring section and an amount of light received by the optical sensor.

FIG. 5 is a graph showing the relationship between the concentration of the platelet in the blood component flowing through the duct 140 and the amount of light (in other words, output voltage) received by the light-receiving element 641. The data shown in the graph was collected in the following condition: wavelength of semiconductor laser: 670 nm, output of laser: 0.8 mW, diameter of laser beams: 1 mm, outer diameter of tube 14: 4.4 mm, thickness of tube 14: 0.7 mm, and interval S: 3.7 mm.

The valves 83–86 are actuated by a driving source such as a solenoid, an electromotive motor, a cylinder (hydraulic or pneumatic) or the like. Tie driving source is actuated based on a signal transmitted thereto from the control section 7 that will be described later. The duct opening/closing means of the present invention is not limited to the valves (cocks), but it is possible to use a clamp that clamps a flexible tube and is capable of sealing the lumen thereof.

The bags 17, 21, 22,104, and 105 are formed by laminating flexible sheets made of resin one upon another and fusing (foe example, thermal fusing, high-frequency fusing) the peripheries thereof or bonding them to each other.

For example Soft polyvinyl chloride is preferably used as the material of the sheet constituting the bags 17, 21, 22, 104, and 105.

As the material of the sheet of the bags 17, 21, 22, 104, and 105, polymerizates formed by polymerization or copolymerization of polyolefins, namely, olefins such as ethylene, propylene, butadiene, isoprene or diolefins.

Preferably, the sheet of the platelet bag 17 is made of a gas-permeable material to preserve the platelet well.

Blood is stored in advance in at least one of the blood bags 104 and 105. Preferably, an anticoagulant such as an ACD-A liquid, a CPD liquid, a CPDA liquid or a heparin sodium liquid is added to the blood stored therein. The number of the blood bags to be installed in the blood storage portion 106 is one or three or more. Blood bag connection methods and blood bag connection patterns are selected as desired. It is possible to use them by aseptically connecting and replacing one or more blood bags with each other by using a tube connection device disclosed in Japanese Utility Model Application Laid-Open No. 6-26877.

The platelet bag 17 may be vacant but may contain a platelet-keeping liquid such as a physiological solution of sodium chloride, GAC, PAS, PSM-1, and the like in advance.

As the material of the tubes 101, 103, 13, 14, 16, 18, 20, 23, and 24, polyvinyl chloride, polyethylene, and the like are used. Polyvinyl chloride is most favorable. The tubes made of polyvinyl chloride are sufficiently flexible and thus can be handled easily and clamped easily with clamps.

As the material of the branch connectors 102, 12, and 15, materials similar to that of the tubes can be used.

The blood component separation apparatus I has the control section 15 (CPU) 7 composed of a microcomputer. The control section 7 has a computing section (in other ,words, information processing means) 71 and a memory 72. The control section 7 is electrically connected with the pump 9, the valves 83–86, the rotation-driving unit 5, the display section 75, and the input section 76. Further, the control section 7 is electrically connected with the optical sensors 61, 62 through signal processing circuits 67, 68, respectively. The number-of-cells measuring apparatus 6 of the present invention includes the tube 14 constituting the duct 140, the optical sensor. 62, the signal processing circuits 67, 68, the control section 7, the display means 75, and the input section 76.

The signal processing circuits 67, 68 convert analog signals transmitted thereto from the optical sensors 61, 62, respectively into digital signals and execute signal processing such as sampling of a signal according to a clock pulse. Signals outputted from the signal processing circuits 67, 68 every predetermined time periods are inputted to the computing section 71. Predetermined signals read, by the memory 72, indicating an discharge amount of the pump 9 and the like are inputted to the computing section 71.

As the display means 75, an emission element array, a liquid crystal display element (LCD), a CRT, and the like can be used. Further, in addition to the display means 75 or instead thereof, information may be made by voice or a printer may be used to print out a display content.

The input section 76 includes an input terminal to which a personal computer, various commanders, and the like can be connected, an operation portion for performing input operation of information, a connection portion of a terminal of an IC memory card, a signal-receiving portion of radio waves (electromagnetic waves) in. radio communication, and a light-receiving portion in optical communication (wire and wireless) in infrared-ray communication. The input section 76 outputs information of the size of the pre-measured platelet (for example, mean platelet volume (MPV) of the pre-measured platelet) and the like measured in advance to the control section 7.

The cells included in the liquid that is measured by the number-of-cells measuring apparatus of this invention and the pie-measured cells are collected from a same donor. In other words, a blood that is measured by the number-of-cells measuring apparatus of this invention and the pre-measured platelet are collected from a same donor.

The information of the size of the platelet includes the information indicating the size of the platelet directly, information of processing thereof, information relevant to the size of the platelet, information specifying the size of the platelet and the like. Thus, the information of the size of the platelet includes for example a correction value y that will be described later.

Signals (information of detected interface position) sent from the optical sensor 61 and signals (information of platelet concentration) sent from the optical sensor 62 are processed by the signal processing circuits 67, 68, respectively and then inputted to the control section 7. Based on the signals sent from the optical sensors 61, 62, the control section 7 controls the rotation/stop of the pump 9, and its rotation direction (forward/backward), and the number of rotations thereof, according to a program stored in the memory 72. The control section 7 also controls the opening/closing of the valves 83–86 and the operation of the rotation-driving unit 5 as necessary. As will be described later, the computing. section 71 determines the number of platelets from the information of the concentration of the platelet sent from the optical sensor 62, the information of an discharge amount of the pump 9 (information corresponding to the flow rate of the blood component flowing through the duct 140 in a surge process which will be described later), and the information of the size of the platelet (mean platelet volume) sent from the input portion 76, thus displaying the number of the platelets on the display means 75.

The measuring apparatus of the invention does not measure the number whose the number of a cell is accurate or strict. The measuring apparatus of the invention measures an about number of the cells. The number of platelets computed by the computing section 71 is a rough estimate value because the computed number of platelets is quite large number and only first several digits are computed out of all digits of the number of platelets. Thereby, the computing function of computing a number of cells installed on the blood component separation apparatus 90 is to compute the rough estimate value of the number of cells.

In the number-of-platelets measuring apparatus 6, a first mode and a second mode can be switched to each other by a mode-switching signal sent to the control section 7 from the input section 76.

In the first mode, in determining the number of platelets, correction is performed by the correction value y that will be described later.

In the second mode, in determining the number of the platelets, correction is not performed by the correction value y that will be described later. In the second mode, the number of the platelets is determined by substituting 1 for y of equations 1, 2.

The method of separating blood components and feeding them by using the blood component separation apparatus 1 shown in FIG. 1 and the operation of the number-of-platelets measuring apparatus 6 of the present invention will be described below.

PREPARATION

Using a sequential multi-channel blood component auto-analyzer (not shown), a mean platelet volume (MPV) is measured for bloods gathered preliminarily before blood is donated from a certain donor and accommodated in the blood bags 104, 105. The obtained value of the mean platelet volume of the blood gathered preliminarily is equal to the size of platelets, namely, the value of the mean platelet volume of the blood donated from the donor and accommodated in the blood bags 104, 105.

When the number-of-platelets measuring apparatus 6 is placed in the first mode, the value (value for the blood bag 104) of an obtained mean platelet volume (measured in advance) is inputted to the input section 76. Thereby, the value of the mean platelet volume is inputted to the control section 7, and the correction value V is set. The correction value y will be described later.

[1] 400 ml of donated blood of the donor is filled into each of the blood bags 104, 105. The pump 9 is actuated (rotated forward) with the tube 103 closed with a clamp, the valves 83, 85 opened, and the other valves closed. Thereby, the blood inside the blood bag 104 is fed through the tubes 101 and 13 and introduced into the rotor 42 from the inflow port 43 of the centrifugal bowl 4 through the tubular member 41. The rotation speed of the pump 9 is so set that the discharge amount of blood (blood supply speed) is 30–80 ml/minute.

[2] Simultaneously with the feeding of the blood of the process [1], the rotation-driving unit 5 is actuated to rotate the rotor 42 at preferably 3000–6000 rpm (for example, 4800 rpm). The blood which has flowed out from the lower-end opening of the tubular member 41 flows radially through the duct 47 toward the periphery of the centrifugal bowl 4 owing to a centrifugal force caused by the rotation of the rotor 42 and is then collected into the blood storage space 46. In the blood storage space 46, the blood is separated into the plasma layer 31, the buffy coat layer 32, and the red blood cell layer 33.

[3] While the processes [1] and [2] are performed continuously, the valve 85 is closed and the valve 86 is opened when the plasma layer 31 has arrived the upper part 45 of the blood storage space 46. Thereby, the plasma inside the rotor 42 overflows from the outflow port 44 and is collected into the plasma bag 21 through the tubes 14, 18, the chamber 19, and the tube 24.

[4] With the exhaust of the plasma from the rotor 42, the interface B between the buffy coat layer 32 and the red blood cell layer 33 rises gradually. The optical sensor 61 always detects the interface B. When the optical sensor 61 detects that the interface B has arrived at a predetermined level (surge start level), the rotation of the pump 9 is stopped under the control of the control section 7, based on a detection signal (information of detected interface position). Thereby, the feeding of the blood and the collection of the plasma are completed.

[5] Then, under the control of the control section 7, the valves 84, 85 are opened, the other valves are closed, the pump 9 is actuated (rotated forward), the connection-side end of the tube 24 of the plasma bag 21 is directed downward, and the plasma inside the plasma bag 21 is supplied to the rotor 42 through the tube 24, the chamber 19, the tubes 20, 13, and the tubular member 41. The plasma which has flowed out from the lower-end opening of the tubular member 41 flows radially through the duct 47 toward the periphery of the centrifugal bowl 4 owing to the centrifugal force caused by the rotation of the rotor 42 and rises inside the blood storage space 46 through the lower portion thereof. Thereby, the platelet inside the buffy coat layer 32 floats upward (fly upward) against the centrifugal force and flows out from the inflow port 44 through the duct 48 together with the plasma, and is then collected into the platelet bag 17 (surge process) through the tubes 14 and 16.

In the surge process, the control section 7 controls the rotation speed (discharge amount of plasma) of the pump 9 and sets the supply speed of the plasma to be supplied to the rotor 42. In this case, the supply speed of the plasma is set to a predetermined value less than 200 ml/minute. During the collection of the platelet, the supply speed of the plasma, namely, the flow rate of the blood component that flows out from the rotor 42 may be appropriately altered. Further, in the surge process, the number of rotations of the rotor 42 may be equal to that in the process [1] or different therefrom.

In the surge process, the optical sensor 62 always measures the concentration of the platelet in the blood component (in other words, plasma including a lot of platelets) which has flowed out from the rotor 42 and is flowing through the duct 140 of the tube 14. Then, the optical sensor 62 sends the computing section 71 of the control section 7 the information of the concentration of the platelet and that of the discharge amount of the pump 9. The computing section 71 determines the total number of platelets as follows: The memory 72 stores the program of the computation for determining the total number of platelets.

The number M of platelets per unit volume is shown by the equation shown below: In the equation 1, A is an output voltage (about 4V in FIG. 5) of the optical sensor 62 when the number of platelets is zero, and a is an actual output voltage of the optical sensor 62 during measurement. In the equation 1, y is the correction value which will be described later, and k is a constant which is experimentally determined for the platelet (for example, mean platelet volume is about 10 fl ($10^{-15}$ liters)) that makes the correction value y about one.

$$M = k \times (A-a)/y \cdots \qquad \text{(equation 1)}$$

In the number-of-cells measuring apparatus 6, a calibration curve for determining the correction value y of the equation 1 from the mean platelet volume sent from the input section 76 is experimentally determined. The calibration curve is stored in the memory 72 in advance as an equation (computation equation) or a table.

The case in which the calibration curve is stored as an equation will be described below.

Supposing that a parameter showing the mean platelet volume (MPV) is x, the correction value y is expressed by a function (approximate polynomial expression) of an n-th degree (n is integers 1 or more) of x.

The above n is favorably, 1–5 and more favorably 3 ($y = ax^3 + bx^2 + cx + d$, where a, b, and c are coefficients and d is a constant).

If the n exceeds the upper limit, it takes much time and labor to set the coefficients and constant of the approximate polynomial expression. On the other hands, if the n is less than the lower limit, the degree of approximation of the approximate polynomial expression is low and the measurement accuracy of the total number of platelets is also low.

The calibration curve, namely, the approximate polynomial expression of the correction value y can be set experimentally as follows:

Predetermined measurement is conducted for blood donated preliminarily to determine a hematocrit value, a platelet concentration (number of platelets per unit amount of blood), and an mean platelet volume (MPV).

Then, based on the obtained hematocrit value and the platelet concentration, the total number of platelets supposed to be collected (supposed total number of platelets) in the blood bag is determined.

Using the blood component separation apparatus 1, the total number of platelets is determined by substituting 1 for y of the equation 2 that will be described later.

Then, the ratio of the obtained total number of platelets to the supposed total number of platelets (total number of platelets/supposed total number of platelets) is determined.

A large number of different donated bloods and bloods preliminarily donated before a large number of the different donated bloods are donated are measured in a manner similar to that described above to collect data.

Then, based on the data, an equation showing the relationship between the ratio of the total number of platelets to the supposed total number of platelets (total number of platelets/supposed total number of platelets) and the mean platelet volume is derived. That is, supposing that the mean platelet volume is set to x and that the ratio of the total number of platelets to the supposed total number of platelets (total number of platelets/supposed total number of platelets) is set to y, an approximate polynomial expression of the correction value y is derived by using x as the parameter.

Needless to say, the method of setting the calibration curve is not limited to the above-described method.

Figure 6:
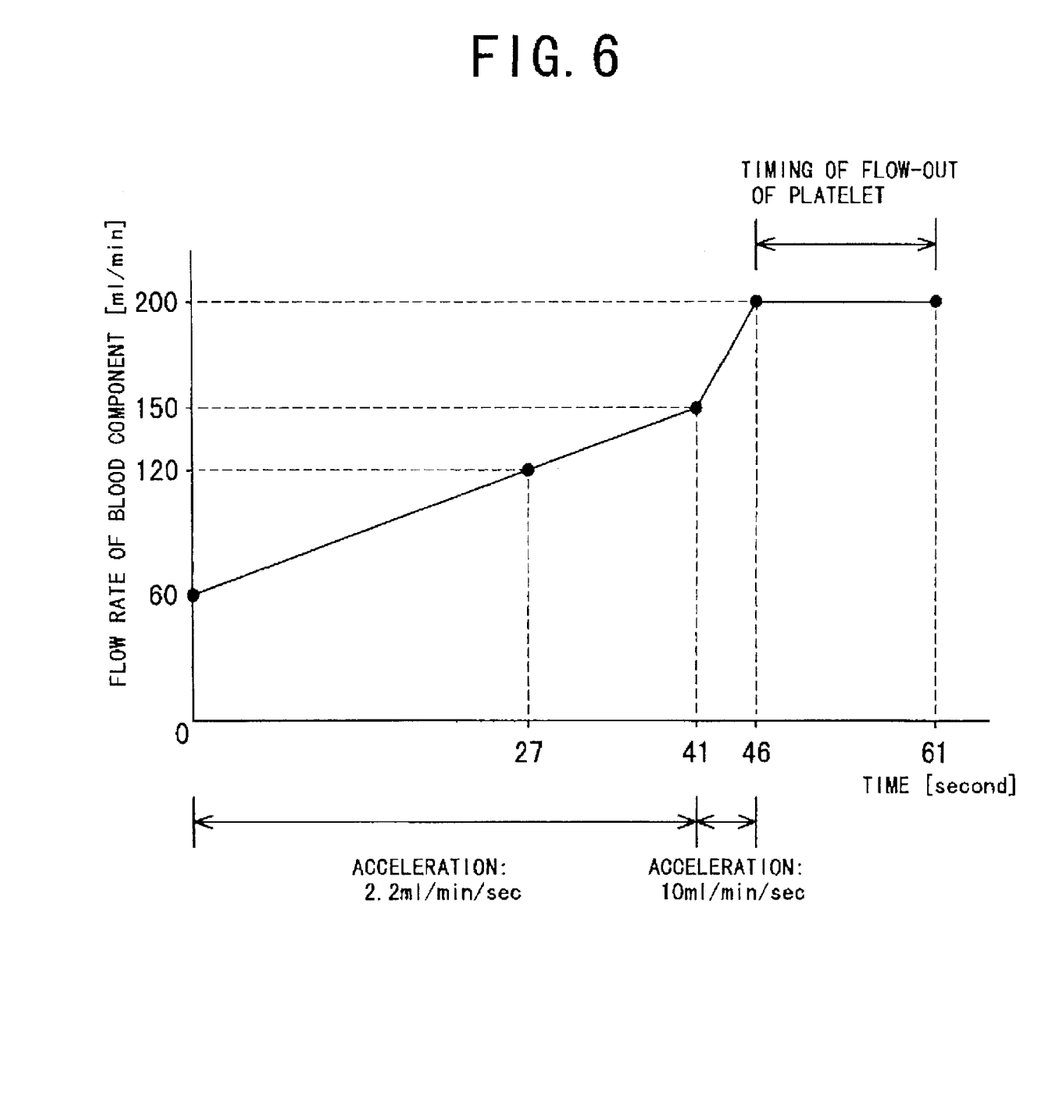
FIG. 6 is a graph showing the change of a flow rate of blood components flowing through a duct relative to the elapse of time in a surge process (platelet collection process).

The flow rate of the blood component flowing through the duct 140 corresponds to the number of rotations (discharge amount) of the pump 9 which supplies plasma to the blood storage space 46. The change of the flow rate of the blood component is expressed by the pattern of FIG. 6. The platelet is collected into the platelet bag 17 during the time period of 46–61 seconds shown in FIG. 6, namely, when the flow rate of the blood component is 200 ml/minute.

The discharge amount (passage amount of blood component in the duct 140) of the blood component per rotation of the pump 9 is a constant that is determined by the configuration of the pump and the size of the pump tube. Supposing that the constant (discharge amount) is set as α; the total number of rotations of the pump 9 while the platelet is being collected into the platelet bag 17 is set as β; and the number of the platelets per unit volume and per rotation of the pump 9 is set as M (n), the total number Plt(β) of platelets to be collected into the platelet bag 17 is expressed by an equation 2 shown below. The M (n) is as shown by the equation 1.

$$Plt(\beta) = \sum_{n=1}^{\beta} M(n) \times \alpha \qquad \text{(Equation 2)}$$

Because α is the known value, a total number N1 of platelets to be obtained by single processing can be determined by monitoring the output voltage (a) of the optical sensor 62 at least every one rotation of the pump 9 and performing computation by substituting an obtained value for the equation 2.

The obtained total number N1 of platelets is displayed on the display means 75.

The measuring apparatus of the invention does not measure the number whose the number of a cell is accurate or strict. The measuring apparatus of the invention measures an about number of the cells. A correction number of platelets computed by the computing section 71 is a rough estimate value because the correction number of platelets is quite large number and only first several digits are computed out of all digits of the number of platelets. Thereby, the computing function of computing the correction number of cells installed on the blood component separation apparatus 90 is to compute the rough estimate value of the correction number of cells.

A total number N3 of platelets to be collected into the platelet bag 17 during the processing can be determined in real time by monitoring an output voltage (a) of the optical sensor 62 for at least every one rotation of the pump 9 and performing computation by substituting an obtained value for the equation 2. The obtained total number N3 of platelets can be displayed on the display means 75 in real time.

Herein, actually, the number of platelets can be determined from the equation 2 by using the equation 1 incorporating the correction value y (mean platelet volume x) as the parameter. Taking another view, the procedure of determining the number of platelets can be described as below.

Initially, the number of platelets at the time when 1 is substituted into y of the equation 2 is determined. The number of platelets is corrected with the correction value y (corrected in consideration of the size of platelet measured in advance). Then, a value obtained by the correction is set to the number of the platelets.

That is, supposing that the number of platelets before the correction is M1 and the number of platelets after the correction is M2, the number M2 of platelets is expressed by an equation shown below 3. The number M1 of platelets is the number of platelets when 1 is substituted into y of the equation 2:

$$M2 = M1/y \qquad \text{(equation 3)}$$

[6] When a predetermined period of time (for example, 120 seconds) elapses after start of supply of plasma, it is determined that the collection of the platelet into the platelet bag 17 has been completed. Then, under the control of the control section 7, the pump 9 is stopped to stop the supply of the plasma into the rotor 42. Then, the rotation-driving unit 5 is stopped. Thereby, the collection of the platelet in the surge process terminates.

[7] The valves 83, 85 are opened, the other valves are closed, and the pump 9 is rotated backward. Thereby, red blood cell, white blood cell, and a small amount of plasma left in the centrifugal bowl 4 are returned to the blood bag 104 through the tubular member 41 and the tubes 13, 101.

After the surge process terminates or thereafter, it is possible that the valves 84, 86 are opened, the other valves are closed, and the pump 9 is rotated forward to supply the plasma in the plasma bag 21 to the rotor 42 through the tube 24, the chamber 19, and the tubes 20, 13; and then, the valves 83, 85 are opened, the other valves are closed, and the pump 9 is rotated backward to return the plasma in the centrifugal bowl 4 fed from the plasma bag 21 to the blood bag 104 through the tubular member 41 and the tubes 13, 101.

[8] A position of the tube 101 located between the branch connector 102 and the blood bag 104 is sealed by fusing and a sealed portion of the tube 101 is cut. Thereby, the blood bag 104 containing blood having a reduced number of platelets to be returned to a donor is obtained. The blood in the blood bag 104 is returned to the donor when necessary.

[9] The value (value for the blood bag 105) of the mean platelet volume is sent to the control section 7 from the input section 76. Thereby, the value of the mean platelet volume is sent to the control section 7 and the correction value y is set. If the value of the mean platelet volume at a first-time processing is equal to that at a second-time processing, the processing is omitted.

The tube 103 is unclamped, the pump 9 is rotated forward, the process [1] is performed, and then, the processes [2]–[7] are performed. Thereby, for the blood gathered in the blood bag 105, the second-time blood collection into the platelet bag 17 and the return of the blood components to the blood bag 105 are accomplished.

In the second-time platelet collection, as described previously, the total number N2 of platelets collected in the first-time processing is determined from the equation 2. Then, the obtained total number N2 of platelets is displayed on the display means 75.

It is possible to display the total N=total number N1 of platelets+total number N2 of platelets on the display means 75.

In the second-time platelet collection, during processing, it is possible to determine a total number N4 of platelets that is collected into the platelet bag 17 from the equation 2 in real time, similarly to the above-described manner. The obtained total number N4 of platelets can be displayed on the display means 75.

It is possible to display the total N5=total number N1 of platelets+total number N4 of platelets on the display means 75 in real time.

[10] The tube 103 is sealed by fusing and a sealed portion of the tube 103 is cut. Thereby, the blood bag 105 containing the blood having a reduced number of platelets to be returned to a donor is obtained. The blood in the blood bag 105 is returned to the donor when necessary.

[11] The tube 16 is sealed by fusing and a sealed portion of the tube 16 is cut. Thereby, the platelet bag 17 containing a platelet product is obtained.

As described above, the number-of-cells measuring apparatus 6 can measure the number of platelets collected into the platelet bag 17 in real time during a blood collecting stage. Accordingly, it is possible to collect a target number (number of units) of platelets in a minimum number of blood-treating times and thus lighten the burden of the donor, save blood to be treated, and reduce a processing time period. Further, the number-of-cells measuring apparatus 6 allows the number of platelets to be measured in a closed system without sampling of collected platelets. Therefore, the number-of-cells measuring apparatus 6 does not have the problem of pollution because penetration of dust and bacteria is prevented and is safe.

In the case where the number of platelets is determined without making correction by using the correction value y and in particular, in the case where platelets are comparatively small (for example, mean platelet volume is less than 9 fl), the measured number of platelets is smaller than that of collected platelets. In the first mode of the number-of-cells measuring apparatus 6, the number of platelets is determined from the equation 2 incorporating the correction value y (mean platelet volume x) as the parameter. Accordingly, irrespective of the size of platelets, it is possible to accurately measure the number of platelets collected in the platelet bag 17. Thereby, in the case where the size of platelets is normal, comparatively large, and comparatively small, it is possible to attain a target number (number of units) of platelets in a minimum number of processing times and thus lighten the burden of the donor, save blood to be treated, and reduce a processing time period.

Figure 7:
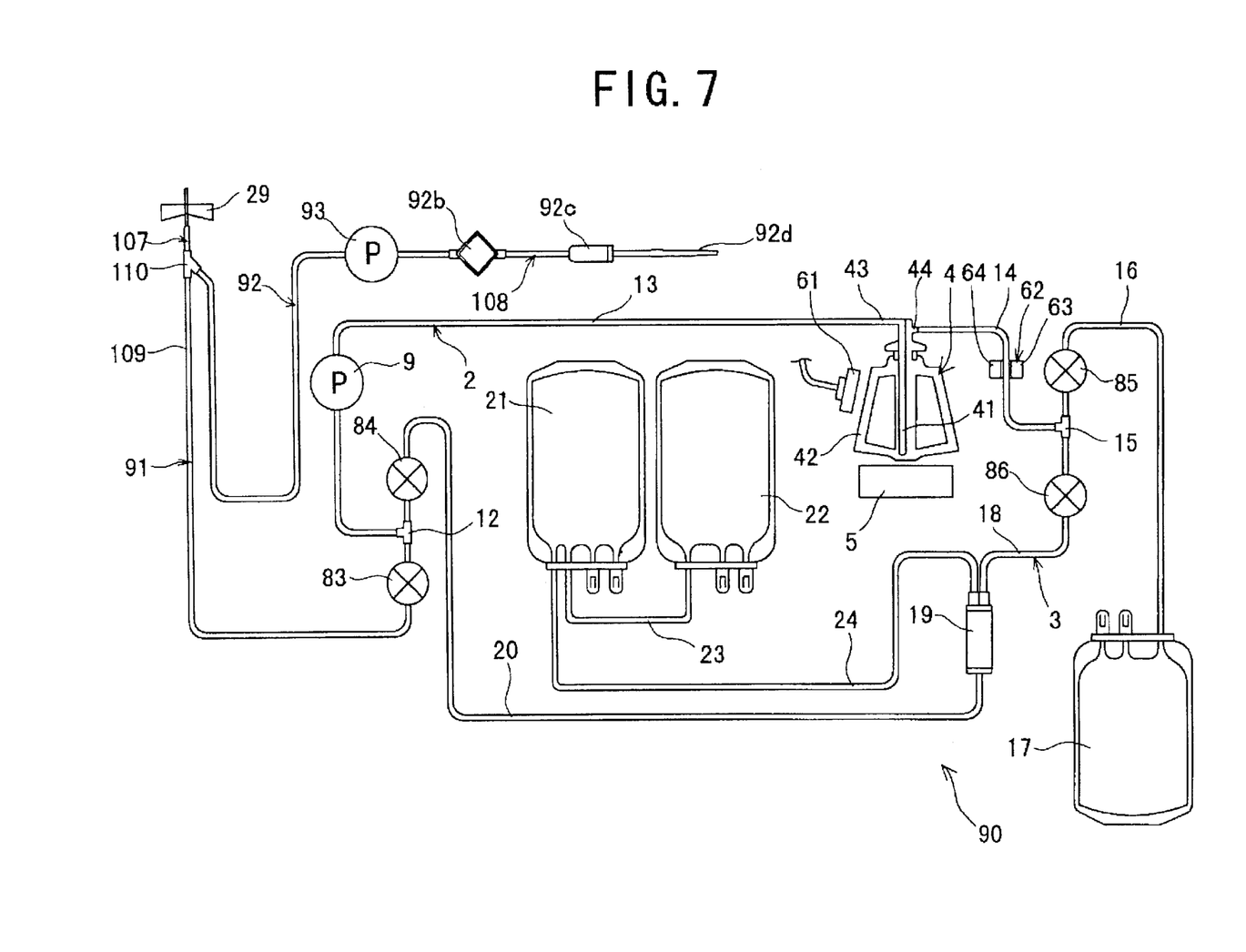
FIG. 7 is a schematic drawing of another example of the construction of a blood component separation apparatus on which the number-of-cells measuring apparatus of the present invention is installed.

Another example of the construction of a blood component separation apparatus on which the number-of-cells measuring apparatus of the present invention is installed will be described below. FIG. 7 is schematic drawing of another example of the construction of a blood component separation apparatus on which the number-of-cells measuring apparatus of the present invention is installed.

The base construction of the blood component separation apparatus 90 and the blood component separation apparatus 1 are same. The blood component separation apparatus 90 includes a blood collector 107 and an anticoagulant injector 108 instead of the blood storage portion 106. Only the constructions of the blood component separation apparatus 90 that are different from the constructions of the blood component separation apparatus 1 will be described below. An explanation of the constructions of the blood component separation apparatus 90 that are the same as the construction of the blood component separation apparatus 1 is omitted.

The blood component separation apparatus 90 includes a centrifugal bowl 4 (in other words, centrifugal separator), a rotation-driving unit 5 for driving the centrifugal bowl, a first line 2 (in other words, line for introducing blood or plasma) for selectively introducing blood and plasma layer into the centrifugal bowl 4, a second line (in other words, blood component collection line) 3 for collecting blood components separated by the centrifugal bowl 4, an optical sensor 61 detecting an interface between the blood components, an optical sensor 62 detecting the concentration of a platelet, a control section (in other words, control means) 7, a third line 91 (in other words, line for donating blood from donor and returning blood thereto) having a blood collector 107, a forth line 92 which branches from the third line 91 and having an anticoagulant injector 108 which injects anticoagulants to collected bloods, a pump 9 installed on the first line 2, a pump 93 installed on the forth line 92 and display section (in other words, display means) 75.

As shown in FIG. 7 the third line 91 includes the tube 109 having the collection needle 29 on the distal end of the third line 91. A known metal needle is used as the blood collection needle 29. The forth line 92 is connected with the third line 91 in the vicinity of the collection needle 29 through a branch connector 110. The forth line 92 has the following elements arranged as viewed from the connector 110, a foreign matter removing filter 92b, a bubble removing chamber 92c, and an anticoagulant container-connecting needle 92d. The pump 93 is installed on the branch connector 110-side as viewed from a foreign matter-removing filter 92b.

The rear end of the tube 91 is connected with one end of the tube 13 and one end of the tube 20 through T-shaped connector 12. A valve 83 serving as a duct opening/closing means for cutting off and releasing an inner duct of the tube 91 is mounted on the tube 91.

As the materials of the tubes 91, 92 and the branch connector 110, polyvinyl chloride, polyethylene, and the like are used. Polyvinyl chloride is most favorable. The tubes made of polyvinyl chloride are sufficiently flexible and thus can be handled easily and damped easily with clamps.

Preferably, an anticoagulant such as an ACD-A liquid, a CPD liquid, a CPDA liquid or heparin sodium liquid is stored in the anticoagulant container (not shown in FIG. 7).

The method of separating blood components and feeding them by using the blood component separation apparatus 90 shown in FIG. 7 and the operation of the number-of-platelets measuring apparatus 6 of the present invention will be described bellow.

PREPARATION

Like the case of the blood component separation apparatus 1 that was mentioned above, a mean platelet volume (MPV) is measured for bloods gathered preliminarily before blood is donated from a certain donor. When the number-of-platelets measuring apparatus 6 is placed in the first mode, the value of an obtained mean platelet volume (measured in advance) is inputted to the control section 7, and the correction value y is set.

First the third line 91 and the blood collection needle 29 are primed with the anticoagulant then the blood collection needle is stuck on the donor. The pump 9 is actuated (rotated forward) with the valves 83, 85 opened and other valves closed. Thereby, the collected blood is fed through the tubes 109 and 13 and introduced into the rotor 42 from the inflow port 43 of the centrifugal bowl 4 through the tubular member 41. The rotation speed of the pump 9 is so set that the discharged amount of blood (blood supply speed) is about 20~100 ml/minutes. At this time, a pump 93 constituting the anticoagulant pump supplies the anticoagulant so set that the discharged amount of anticoagulant is about 1.0~12.5 ml/minutes. Thereby the collected blood from donor is mixed with ACD-A liquid (anticoagulant) and is fed through the tubes 109 and 13. The collected blood is introduced into the rotor 42 from the inflow port 43 of the centrifugal bowl 4 through the tubular member 41. Then above-mentioned processes [2]~[6] are performed. The obtained total number N1 of platelet can be displayed on the display means 75.

The valves 83, 85 are opened, the other valves are closed, the forth tube 92 is closed with a clamp and the pump 9 is rotated backward. Thereby, red blood cell, white blood cell, and a small amount of plasma left in the centrifugal bowl 4 are returned to the donor through the tubular member 41, the tubes 13, 109 and the blood collection needle 29. The rotation speed of the pump 9 is so set that the discharged amount of blood (blood supply speed) is about 20~100 ml/minutes.

After the surge process terminates or thereafter, it is possible that the valves 84, 86 are opened, the other valves are closed, and the pump 9 is rotated forward to supply the plasma in the plasma bag 21 to the rotor 42 through the tube 24, the chamber 19 and the tubes 20, 13. Then, the valves 83, 85 are opened, the Other valves are closed, and the pump 9 is rotated backward to return the plasma in the centrifugal bowl 4 fed from the plasma bag 21 to the donor through the tubular member 41 and the tubes 13, 109.

The tube 16 of the vicinity of the platelet bag 17 is sealed by fusing and a sealed portion of the tube 16 is cut. Thereby, the platelet bag 17 containing a platelet product is obtained. As described later, if a second-time platelet collection processing is performed, the tube 16 is not sealed and cut.

When necessary, the pump 9 is rotated forward, the second-time platelet collection processing is performed. The second-time platelet collection processing is similar to above-mentioned processing of the blood component separation apparatus 90 containing the process [2]~[6] of the blood component separation apparatus 1.

In the second-time platelet collection, as described previously, the total number N2 of platelets collected in the first-time processing is determined from the equation 2. Then, the obtained total number N2 of platelets is displayed on the display means 75.

It is possible to display the total N=total number N1 of platelets+total number N2 of platelets on the display means 75.

In the second-time platelet collection, during processing, it is possible to determine a total number N4 of platelets that is collected into the platelet bag 17 from the equation 2 in real time, similarly to the above-described manner. The obtained total number N4 of platelets can be displayed on the display means 75. It is possible to display the total N5=total number N1 of platelets+total number NA of platelets on the display means 75 in real time.

If the platelet collection process terminates after the second-time platelet collection processing, the tube 16 is sealed by fusing and a sealed portion of the tube 16 is cut. If the third-time platelet collection processing is performed, the tube 16 is not fused and cut. The third-time platelet collection processing is similar to above-mentioned processing of the blood component separation apparatus 90 containing the process [2]~[6] of the blood component separation apparatus 1. Thereby, red blood cell, white blood cell, and a small amount of plasma left in the centrifugal bowl 4 are returned to the donor through the tubular member 41 ,the tubes 13, 109 and the blood collection needle 29. The tube 16 of the vicinity of the platelet bag 17 is sealed by fusing and a sealed portion of the tube 16 is cut. Thereby, the platelet bag 17 containing a platelet product is obtained.

In the third-time platelet collection, as described previously, the total number N2 of platelets collected in the first-time processing is determined from the equation 2. Then, the obtained total number N2 of platelets is displayed on the display means 75.

It is possible to display the total N=total number N1 of platelets+total number N2 of platelets on the display means 75.

In the third-time platelet collection, during processing, it is possible to determine a total number N4 of platelets that is collected into the platelet bag 17 from the equation 2 in real time, similarly to the above-described manner. The obtained total number N4 of platelets can be displayed on the display means 75. It is possible to display the total N5=total number N1 of platelets+total number N4 of platelets on the display means 75 in real time.

EXAMPLES

The examples of the number-of-cells measuring apparatus of the present invention are described below.

First Example

Measurement was conducted for blood obtained in a preparatory blood collection to determine a hematocrit value, a platelet concentration (number of platelets per unit amount of bloods), and a mean platelet volume (MPV).

The obtained value of the platelet concentration was set as a supposed Plt concentration.

Then, the number of processing times (number of blood bags) necessary for collecting the platelet was determined from the hematocrit value.

A supposed total number of the platelets to be collected into the platelet bag was determined from the obtained supposed Plt concentration, the number of processing times (three times), and the amount of blood per blood bag. The value was set to the supposed Plt.

Then, blood was donated from the donor, and the gathered blood was filled into the blood bag. Then, using the blood component separation apparatus (shown in FIG. 1) having the number-of-cells measuring apparatus of the present invention installed thereon, the mode of the number-of-cells measuring apparatus was set to the first mode, the value of the obtained mean platelet volume was sent to the control section from the input section, the platelet was collected (returned) into the platelet bag in the above-described procedure, and the total number of the collected platelets was measured. The value of total number of the collected platelets was set to Plt.

The correction value y of the equations 1, 2 is shown in an equation 4 below:

$$y=(0.2185x^3-7.8245x^2+94.114x-276.86)/100\cdots \quad \text{(equation 4)}$$

The equation 1 is as follows:

$$M=k \times (A-a)/y \cdots \quad \text{(equation 1)}$$

Then, sampling was conducted for platelets collected in the platelet bag. The number of the platelets was measured by using Sysmex NE6000 manufactured by Sysmex Inc. The total number of the collected platelets was determined from the measured number of the platelets. The value of total number of the collected platelets was set to Plt.

First Comparison Example

The mode of the number-of-cells measuring apparatus was set to the second mode. Correction was not made by using the correction value y of the equations 1, 2. Each measurement was conducted in a manner similar to that of the first example.

Second Example

Except that the mean platelet volume was different from that of the first example, each measurement was conducted in a manner similar to that of the first example.

Second Comparison Example

The mode of the number-of-cells measuring apparatus was set to the second mode. Correction was not made by the use of the correction value y of the equations 1, 2. Each measurement was conducted in a manner similar to that of the second example.

The result of each of the first example, the second example, the first comparison example, and the second comparison example is shown in table 1 below.

TABLE 1

|  | First E | First CE | Second E | Second CE |
| --- | --- | --- | --- | --- |
| Hematcrit value | 44.6 | 44.6 | 37.1 | 37.1 |
| Supposed Plt concentration ($10^4$/ml) | 29.1 | 29.1 | 39.9 | 39.9 |
| Mean platelet volume (fl) | 10.1 | 10.1 | 8.1 | 8.1 |
| Treating times | 3 | 3 | 3 | 3 |
| Supposed Plt ($\times 10^{11}$) | 2.09 | 2.09 | 3.6 | 3.6 |
| Displayed Plt ($\times 10^{11}$) | 2.07 | 2.08 | 3.6 | 3.18 |
| Collected Plt ($\times 10^{11}$) | 2.19 | 2.19 | 3.74 | 3.74 |

Where E is example and CE is comparison example.

<Examination of Result>

In the first example and the first comparison example in which the mean platelet volume is 10.1 (fl), the displayed Plt is very close to the collected Plt.

In the second example in which the mean platelet volume is 8.1 (fl), the displayed Plt is very close to the collected Plt. On the other hand, in the second comparison example in which the mean platelet volume is also 8.1, the displayed Plt is determined without considering the mean platelet volume. Thus, in the second comparison example, the displayed Plt is much smaller than the collected Plt.

That is, according to the present invention, the displayed Plt is determined by considering the mean platelet volume. Thus, regardless of whether the mean platelet volume is large or small, it is possible to correctly determine the displayed Plt.

Although the embodiment of the number-of-cells measuring apparatus of the present invention has been described with reference to the drawings, the present invention is not limited thereto but each part can be replaced with any desired part having a similar construction.

For example, needless to say, the method of computing the number of platelets (cells) in the first mode is not limited to the above-described one but any desired methods can be employed, so long as they use the flow rate of the blood component (liquid to be examined), the platelet concentration (concentration of cell), and the size of platelet (cell) preliminarily measured or a numerical value in which the size of platelets is considered.

The optical sensor (measuring section) 62 may be installed at other positions, for example, on the tube 16.

In the above-described embodiment, the flow rate of the blood component flowing through the duct 140 is grasped as the discharge amount of the ump 9 in the surge process. But a flow meter may be installed on the tube 13, 14 or 16 to use information obtained by the flow meter.

The number-of-cells measuring apparatus of the present invention is installed on the blood component separation apparatus. However, the number-of-cells measuring apparatus may be installed on other apparatuses or used independently.

The present invention is not limited to measurement of the number of platelets, but is applicable to that of the number of white blood cells, red blood cells, and other cells.

In the embodiment, the concentration of cells is measured by the optical sensor (measuring section) but if a liquid to be examined is electrolytic, a cell concentration can be measured by measuring its electrical conductivity.

Further, it is possible to provide a plurality of measuring sections along the duct to utilize each of values measured by respective measuring sections or a mean value thereof for computation of the number of platelets.

The present invention is so constructed that based on a determined number of platelets, the operation of the blood component separation apparatus can be controlled. For example, it is possible to accomplish an automatic control of shifting a platelet collection operation to a blood return operation when the number of platelets to be collected into the platelet bag 17 reaches a target value.

According to the present invention, a personal computer may determine the correction value y from the mean platelet volume, and the correction value y may be inputted to the number-of-cells measuring apparatus from the personal computer.

According to the present invention, the information of the size (or a value in which the size is considered) of platelets (cells) may be inputted to the number-of-cells measuring apparatus by wire or wireless communication from the personal computer or various commanders.

In the present invention, the second mode may not be provided.

As described above, the number-of-cells measuring apparatus can measure the number of cells in real time. Accordingly, it is possible to know the number of collected platelets during a blood treating operation in manufacturing a platelet product. Thereby, it is possible to attain a target number of platelets in a minimum number of blood-treating times and thus lighten the burden of the donor, save blood to be treated, and reduce a blood-treating time period.

In particular, the number of cells is determined based on the flow rate of a liquid (blood) to be examined, the concentration of cells, and a pre-measured size of cells or numerical values in which the size thereof is considered (the number of cells is determined based on the flow rate of liquid (blood) to be examined and the concentration of cells, and then correction is made in consideration of pre-measured size of cells). Therefore, irrespective of whether cells are large or small, it is possible to measure the number of cells in real time with high accuracy.

Further, the number-of-cells measuring apparatus allows the number of cells such as platelets to be measured in a closed system without sampling them. Therefore, the number-of-cells measuring apparatus prevents change of their properties and quality deterioration because they are not exposed to air. Further, the number-of-cells measuring apparatus does not have the problem of pollution because penetration of dust and bacteria is prevented.

Furthermore, the measuring section is composed of the optical sensor having the light-projecting portion and the light-receiving portion. In particular, the duct between the light-projecting portion and the light-receiving portion is flat or oval. Thus, it is possible to measure the concentration of cells and the number thereof with high accuracy.

What is claimed is:

1. A number-of-cells measuring apparatus for measuring the number of platelets of-blood components flowing out from an outflow port of a centrifugal separator of a blood component separation apparatus that includes said centrifugal separator, for centrifugally separating a blood into a plurality of said blood components, comprising a rotatable rotor having a blood storage space formed therein and an inflow port and said outflow port both communicating with said blood storage space into which said blood is introduced from said inflow port, a rotation-driving unit for driving said centrifugal separator, a first line for selectively introducing blood and plasma into said centrifugal separator, a second line for collecting blood components separated by said centrifugal separator and including a plasma bag and a platelet bag, with the second line communicated with said first line, a third line having a blood collector and communicating with said first line and said second line, and performing two times platelet collection processing including blood collection from a donor using said blood collector, plasma collection in said plasma bag from said collected blood using said centrifugal separator, platelet collection in said platelet bag using said centrifugal separator and said collected plasma supplied to said centrifugal separator from plasma bag, and blood left in said centrifugal separator returned to said donor, comprising:
- an input section for inputting information of a size of pre-measured platelets;
- a measuring section installed on said second line and measuring a concentration of said platelets of said blood components flowing through said second line; and
- an information processing section processing information of the size of said pre-measured platelets inputted thereto from said input section, information of a flow rate of said blood components flowing through said second line, and information of the concentration of said platelets obtained at said measuring section,
- wherein said information processing section has a function of computing the number of platelets which have passed through said measuring section, based on the flow rate of said blood components, the concentration of said platelets, and the size of said pre-measured platelets or a numerical value in which the size of said pre-measured platelets is considered.

2. A number-of-cells measuring apparatus according to claim 1, further comprising a liquid-feeding means for feeding said liquid to said second line and an amount of said liquid fed by said liquid-feeding means is set as information of the flow rate of said liquid flowing through said second line.

3. A number-of-cells measuring apparatus according to claim 1, wherein said blood and said pre-measured platelets are collected from a same donor.

4. A number-of-cells measuring apparatus according to claim 1, wherein said blood components includes a plurality of platelets and said function of computing the number of platelets computes a rough estimate value of number of platelets.

5. A number-of-cells measuring apparatus according to claim 1, wherein said measuring section is composed of an optical sensor having a light-projecting part and a light-receiving part opposed to said light-projecting part, with said second line interposed therebetween and outputs an electric signal corresponding to an amount of light received by said light-receiving part through said second line.

6. A number-of-cells measuring apparatus according to claim 1, further comprising a display means displaying a measured result.

7. A number-of-cells measuring apparatus for measuring the number of platelets of blood components flowing out from an outflow port of a centrifugal separator of a blood component separation apparatus that includes said centrifugal separator, for centrifugally separating a blood into a plurality of said blood components, comprising a rotatable rotor having a blood storage space formed therein and an inflow port and said outflow port both communicating with said blood storage space into which said blood is introduced from said inflow port, a rotation-driving unit for driving said centrifugal separator, a first line for selectively introducing blood and plasma into said centrifugal separator, a second line for collecting blood components separated by said centrifugal separator and including a plasma bag and a platelet bag and communicating with said first line, a third line having a blood collector and communicating with said first line and said second line, and performing two times platelet collection processing including blood collection from a donor using said blood collector, plasma collection in said plasma bag from said collected blood using said centrifugal separator, platelet collection in said platelet bag using said centrifugal separator and said collected plasma supplied to said centrifugal separator from said plasma bag, and blood left in said centrifugal separator returned to said donor, comprising:
- an input section for inputting information of a size of pre-measured platelets;
- a measuring section installed on said second line and measuring a concentration of said platelets of said blood components flowing through said second line; and
- an information processing section processing information of the size of said pre-measured platelets inputted thereto from said input section, information of a flow rate of said blood components flowing through said second line, and information of the concentration of said platelets obtained at said measuring section,
- wherein said information processing section has a computing function of computing a prior-to-correction number of platelets which have passed through said measuring section, based on the flow rate of said blood components and the concentration of said platelets; and a correction value computing function of correcting a prior-to-correction number of said platelets computed by said computing function by taking the size of pre-measured platelets into consideration.

8. A number-of-cells measuring apparatus according to claim 7, wherein said blood and said pre-measured platelets are collected from a same donor.

9. A number-of-cells measuring apparatus according to claim 7, wherein said blood components include a plurality of platelets and said function of computing the number of platelets computes a rough estimate value of number of platelets.

10. A number-of-cells measuring apparatus according to claim 7, wherein said measuring apparatus measures the number of platelets which have flowed out from said outflow port together with plasma by rotating said rotor and supplying plasma to a lower part of said blood storage space having a plurality of said blood components therein.

11. A number-of-cells measuring apparatus according to claim 10, wherein an amount of said plasma supplied to said blood storage space is set as information of the flow rate of said blood components flowing through said second line.

12. A number-of-cells measuring apparatus according to claims 7, wherein said measuring section is composed of an optical sensor having a light-projecting part and a light-receiving part opposed to said light-projecting part, with said second line interposed therebetween and outputs an electric signal corresponding to an amount of light received by said light-receiving part through said second line.

13. A number-of-cells measuring apparatus according to claim 7, further comprising a display means displaying a measured result.

14. A blood component separation apparatus comprising
a centrifugal separator for centrifugally separating a blood into a plurality of said blood components comprising a rotatable rotor having a blood storage space formed therein and an inflow port and an outflow port both communicating with said blood storage space into which said blood is introduced from said inflow port,
a rotation-driving unit for driving said centrifugal separator,
a first line to selectively introduce blood and plasma into said centrifugal separator,
a second line to collect blood components separated by said centrifugal separator and including a plasma bag and a platelet bag, the second line communicating with said first line,
a third line having a blood collector and communicating with said first line and said second line,
said blood component separation apparatus performing two times platelet collection processing including blood collection from a donor using said blood collector, plasma collection in said plasma bag from said collected blood using said centrifugal separator, a platelet collection in said platelet bag using said centrifugal separator and said collected plasma supplied to said centrifugal separator from plasma bag, and blood left in said centrifugal separator returned to said donor, and
a number-of-cells measuring apparatus for measuring the number of platelets of blood components flowing out from the outflow port of said centrifugal separator, said number-of-cells measuring apparatus comprising:
an input section for inputting information of a size of pre-measured platelets;
a measuring section installed on said second line and measuring a concentration of said platelets of said blood components flowing through said second line;
an information processing section processing information of the size of said pre-measured platelets inputted thereto from said input section, information of a flow rate of said blood components flowing through said second line, and information of the concentration of said platelets obtained at said measuring section; and
said information processing section being adapted to compute the number of platelets which have passed through said measuring section based on the flow rate of said blood components, the concentration of said platelets, and the size of said pre-measured platelets or a numerical value in which the size of said pre-measured platelets is considered.

15. A blood component separation apparatus comprising
a centrifugal separator for centrifugally separating a blood into a plurality of said blood components comprising a rotatable rotor having a blood storage space formed therein and an inflow port and an outflow port both communicating with said blood storage space into which said blood is introduced from said inflow port,
a rotation-driving unit adapted to drive said centrifugal separator,
a first line to selectively introduce blood and plasma into said centrifugal separator,
a second line to collect blood components separated by said centrifugal separator and including a plasma bag and a platelet bag, the second line communicating with said first line,
a third line having a blood collector and communicating with said first line and said second line,
said blood component separation apparatus performing two times platelet collection processing including a blood collection from a donor using said blood collector, a plasma collection in said plasma bag from said collected blood using said centrifugal separator, a platelet collection in said platelet bag using said centrifugal separator and said collected plasma supplied to said centrifugal separator from said plasma bag, and blood left in said centrifugal separator to said donor, and
a number-of-cells measuring apparatus for measuring the number of platelets of blood components flowing out from the outflow port of said centrifugal separator, said number-of-cells measuring apparatus comprising:
an input section to input information regarding a size of pre-measured platelets;
a measuring section installed on said second line to measure a concentration of said platelets of said blood components flowing through said second line;
an information processing section to process information of the size of said pre-measured platelets inputted thereto from said input section, information of a flow rate of said blood components flowing through said second line, and information of the concentration of said platelets obtained at said measuring section; and
said information processing section being adapted to compute a prior-to-correction number of platelets which have passed through said measuring section based on the flow rate of said blood components and the concentration of said platelets; and to compute a prior-to-correction number of said platelets computed by said computing function by taking the size of said pre-measured platelets into consideration.

* * * * *

UNITED STATES PATENT AND TRADEMARK OFFICE
CERTIFICATE OF CORRECTION

PATENT NO. : 6,678,040 B1 Page 1 of 1
DATED : January 13, 2004
INVENTOR(S) : Atsushi Suzuki It is certified that error appears in the above-identified patent and that said Letters Patent is hereby corrected as shown below:

Column 2,
Line 37, "Wherein" should be -- wherein --.

Column 4,
Line 44, "1motor" should be -- motor --.

Column 6,
Line 55, "22,104" should be -- 22, 104 --.

Column 7,
Line 23, "apparatus I" should be -- apparatus 1 --.
Line 24, "section 15" should be -- section --.
Line 65, "pie-measured" should be -- pre-measured --.

Column 14,
Line 44, "damped" should be -- clamped --.

Column 19,
Line 12, "of-blood" should be -- of blood --.
Line 25, "communicated" should be -- communicating --.

Column 22,
Line 33, "separator to" should be -- separator returned to --.

Signed and Sealed this

Sixth Day of June, 2006

JON W. DUDAS
*Director of the United States Patent and Trademark Office*